United States Patent
Sun et al.

(10) Patent No.: US 6,847,844 B2
(45) Date of Patent: Jan. 25, 2005

(54) METHOD OF DATA COMMUNICATION WITH IMPLANTED DEVICE AND ASSOCIATED APPARATUS

(75) Inventors: Mingui Sun, Pittsburgh, PA (US); Robert J. Sclabassi, Pittsburgh, PA (US); Marlin H. Mickle, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 10/164,517

(22) Filed: Jun. 6, 2002

(65) Prior Publication Data

US 2003/0229382 A1 Dec. 11, 2003

(51) Int. Cl.$^7$ ................................................. A61N 1/36
(52) U.S. Cl. ............................ 607/32; 607/60; 128/903
(58) Field of Search ............................ 607/30, 32, 60; 128/903

(56) References Cited

U.S. PATENT DOCUMENTS

| | | | |
|---|---|---|---|
| 6,076,016 A | * | 6/2000 | Feierbach .................... 607/32 |
| 6,167,310 A | * | 12/2000 | Grevious ..................... 607/32 |
| 6,289,237 B1 | * | 9/2001 | Mickle et al. .............. 600/509 |
| 6,754,472 B1 | | 6/2004 | Williams et al. ............ 455/100 |

* cited by examiner

Primary Examiner—Carl Layno
(74) Attorney, Agent, or Firm—Arnold B. Silverman; Eckert Seamans Cherin & Mellott, LLC

(57) ABSTRACT

Apparatus and method of communicating data employing current pulses transmitted by an implanted device through living biological tissue to an external device. The method also contemplates transmission of current pulses from the external device through living biological tissue to an implanted device. Uniquely configured antenna electrodes are preferably employed in the implanted device. Increase in signal-to-noise ratio is achieved through synchronization. The method may be employed in diagnostic, therapeutic and general monitoring activities in connection with human beings.

39 Claims, 6 Drawing Sheets

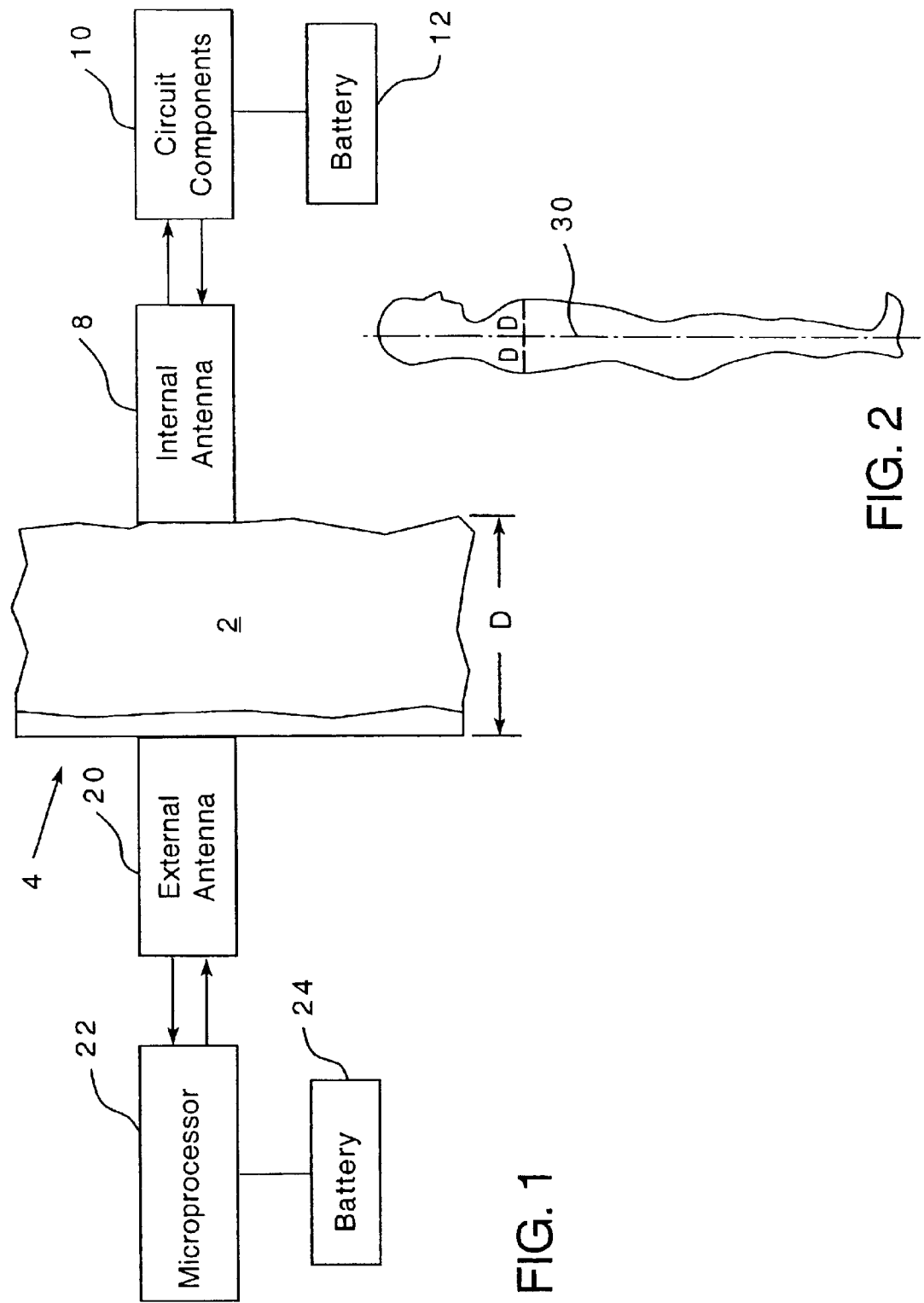

METHOD OF DATA COMMUNICATION WITH IMPLANTED DEVICE AND ASSOCIATED APPARATUS

STATEMENT OF GOVERNMENT INTEREST

The United States Government has rights under this invention pursuant to Grant 1-R01-NS43791 from the National Institutes of Health.

BACKGROUND OF THE INVENTION

1. Field of the Invention

The present invention relates to a method and associated apparatus employed in wireless two-way communication of data by means of current pulses traveling through living biological tissues and, more specifically, it contemplates the use of an implantable device which may be implanted, for example, in a patient's brain, torso or abdomen in cooperation with an external computerized device for diagnostic, monitoring or therapeutic purposes.

2. Description o the Prior Art

The value of using invasive procedures and devices in diagnosing, monitoring or treating patients has long been known in the medical environment. It has been known, for example, to employ a pacemaker for regulating heart functions. Also, deep brain electrical stimulation for the treatment of Parkinson's Disease has been known.

It has also been known to suggest the use of implantable devices which are in communication with an external computerized device, such as by radio frequency (RF) signals or light or wired connection, for example.

It has also been known for various purposes to suggest two-way communication with wireless base and remote stations wherein data may be communicated. See, for example, U.S. Pat. No. 6,289,237.

Among the problems with the prior art utilizing wired systems are the risk of infection and reduced mobility of the patient.

Among the problems with prior art RF systems have been the requirement for substantial size, difficulty in recharging batteries and signal-to-noise ratio. Also the energy required to convert between the signal and the RF waves can be substantial.

There remains, therefore, a substantial need for an implantable device which will efficiently and accurately receive signals from an external device and deliver signals to the external device for medical diagnosis, monitoring and therapeutic purposes.

SUMMARY OF THE INVENTION

The present invention has met the above-described need. In the method of the present invention, an implanted device has a first antenna having a pair of electrodes and associated first circuit components. An external device has a second antenna having a pair of electrodes and an associated microprocessor. The invention involves transmitting current pulses containing data through living biological tissue, thereby taking advantage of the electrical conductivity of the ionic fluid of such biological tissue. The data transmission may be effected in both directions, i.e., from the external device to the internal device and from the internal device to the external device. The transmissions are preferably synchronously effected. Corresponding apparatus is provided.

A unique construction of first or volume conduction antenna facilitates directional delivery of the information with high efficiency in the far field.

The efficiency of data communication is such as to enhance battery life. The system also facilitates miniaturization, including the use of microchip technology.

It is an object of the present invention to provide a method and associated apparatus for providing efficient communication between an implanted device and an external device for purposes of data transmission employing volume conduction.

It is another object of the present invention to provide such a system which can be miniaturized and make efficient use of energy employed to power the system.

It is a further object of such an invention which facilitates implantation of the implantable device in a human patient in regions such as the brain, torso or abdomen.

It is yet another object of the present invention to provide such a system which does not require the use of wires for purposes of power delivery or data transmission or the use of light, magnetic field, ultrasound or RF energy.

It is a further object of the present invention to provide such a system which takes advantage of the electrical current carrying capabilities of the body's ionic fluid in order to employ the same as an information carrier.

It is yet another object of the present invention to provide such a system which facilitates efficient synchronous communication of current pulses through living biological tissues.

These and other objects of the invention will be more fully understood from the following detailed description of the invention on reference to the illustrations appended hereto.

BRIEF DESCRIPTION OF THE DRAWINGS

FIG. 1 is a schematic illustration showing the general interaction between the implantable device and the external device.

FIG. 2 is a schematic illustration of a human patient.

DESCRIPTION OF THE PREFERRED EMBODIMENTS

Figure 3:
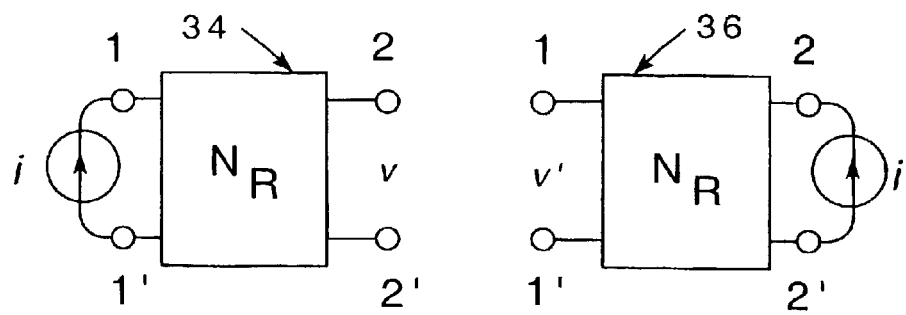
FIG. 3 is an illustration of a passive two-port system illustrating the reciprocity theorem.

As used herein, the term "volume conduction" means data communication by wireless passage of data by current pulses passing through living biological tissues between an implanted device and an external device.

As used herein, the term "patient" means a member of the animal kingdom, including human beings.

As employed herein, the term "current pulse(s)" means electrical current waveforms which have been modified to carry information such as by, for example, phase shift keying, amplitude modulation or frequency modulation.

The present invention makes advantageous use of an implanted device having a first antenna having a pair of electrodes for receiving and transmitting current pulses from and to an external device having a second antenna having a pair of electrodes and employing the external second antenna to deliver and receive current pulses to and from the implanted first antenna. Each antenna is associated with a microprocessor and related circuit components.

The use of suitably processed current to deliver pulsed current information eliminates a number of the aforementioned problems. In the present context, passage of the current pulses which may be made to contain the desired information as by modulation through living biological tissues takes advantage of the fact that ionic fluid in biological tissues conducts electric current efficiently. This, therefore, prolongs the life of and reduces the size of any battery that would be employed in the implantable device. It also eliminates the need for conversion of light, sound, or RF signals to digital signals for purposes of data communication.

This further permits miniaturization which facilitates the use of microelectronic chips, as in implantable brain devices of the present invention.

Referring to FIG. 1, there is shown a segment of living biological tissue 2 such as provided in a patient and skin 4 disposed exteriorly thereof. An internal volume conduction first antenna 8 is in intimate contact with the living biological tissue 2 and is operatively associated with circuit components 10 which may be energized by battery 12 or another device that produces electrical current. The implanted antenna 8, circuit components 10 and battery 12 may all be provided within a single housing (not shown) which may be suitable protectively encapsulated within a biocompatible resinous material such as epoxy or other synthetic material having the desired durability, sealing properties and inertness. The external second antenna 20 is in operative association with a microprocessor 22 which is energized by a suitable power source, which may be a suitable battery 24.

In general, the system, in a manner to be described hereinafter in detail, contemplates two-way communication employing current pulses traveling between the external second antenna 20 and the implanted first antenna 8 in either direction in synchronized fashion. The circuit components 10 may include sensors to obtain information for delivery to the external device and, where appropriate, actuators and other elements desired for the particular use. The present invention eliminates the need to rely on hard wired systems, transmitted energy as by light, sound, or RF and employs the biological tissue electric conductivity characteristics to carry current pulses which contain the desired information.

As shown in FIG. 2, a centerline of a standing human being has been identified as 30 with the dimension D between the outermost portion of the internal first antenna 8 and the innermost portion of the external second antenna 20 which will generally be in contact with skin 4 being designated by the letter "D." In humans, it is presently preferred that the distance "D" be less than about 15 cm. In general, this dimensional preference will be adequate to employ an implanted device within the human brain, torso, or abdomen, as well as other portions of the body, and will be able to communicate with an external device with adequate signal strength for effective communication.

Referring to FIG. 3, there is illustrated a linear two-port network NR with two different connections. It will be seen that, in accordance with the reciprocity theorem these portions which are representative of the antennas 8, 20 have port 34 providing a current source i at terminals 1–1' which produces an open circuit voltage at 2–2' of v. Similarly, port 36 has a current source i which is identical to that for port 34, but at terminals 2–2' and produces an open circuit voltage at terminals 1–1' of v'. Under the reciprocity theorem, v=v' regardless of the topology within $N_R$. This means that the input and output of the system can be interchanged without altering the response of the system to a given waveform. In the present environment this means that reversing the transmission/reception modes of the internal first volume conduction antenna 8 and the external second antenna 20 the received voltage will not vary. As a result, under the same excitation current, the volume conduction based data communication system produces the same output regardless of whether the information is flowing from the external device to the internal device or in the reverse direction.

Referring to FIGS. 4 through 8, a preferred form of first volume conduction antenna of the present invention will be considered.

Figure 4:
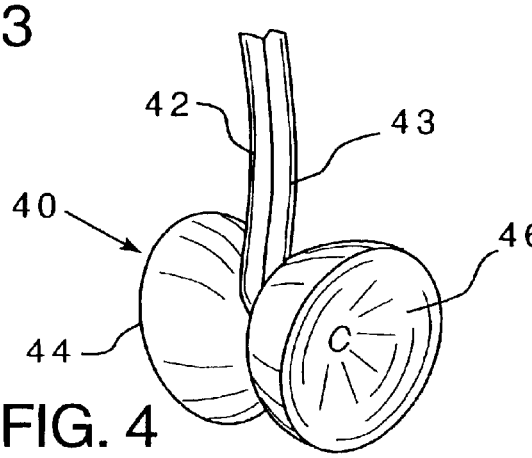
FIG. 4 is a perspective view of a form of preferred volume conduction antenna of the present invention.
Figure 6:
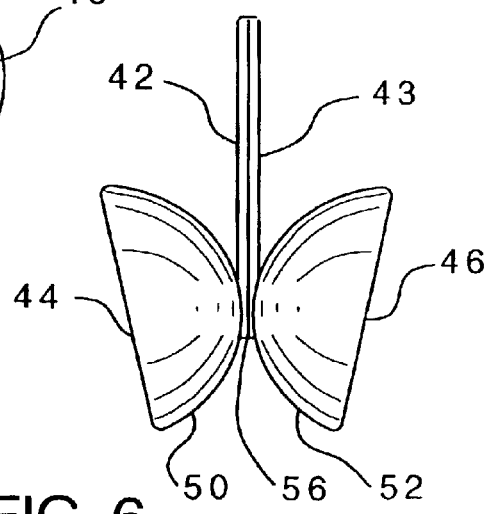
FIG. 6 is a left side elevational view of the antenna as shown in FIG. 5.
Figure 5:
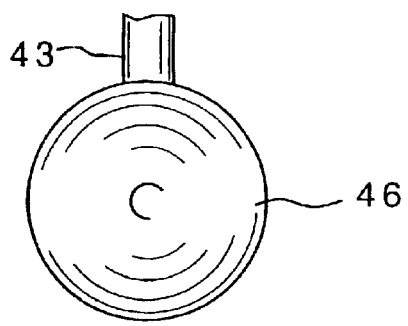
FIG. 5 is an end elevational view of the volume conduction antenna of FIG. 4.

As shown in FIGS. 4 through 6, the preferred first antenna 40 has a suitable electrical connection through wires 42, 43 to other circuit components 10 (not shown in this view) and has a pair of concave shells 44, 46 facing outwardly in generally opposed directions. Shells 44, 46 have inner generally convex surfaces 50, 52, respectively, which in the form shown, are joined at 56. The shells are preferably made of a corrosion resistant metallic or nonmetallic electrically conductive material, such as a suitable metal such as stainless steel or brass, carbon or a conductive polymer, for example, and have on their convex surfaces 50, 52 a coating of an electrically insulating material.

Figure 7:
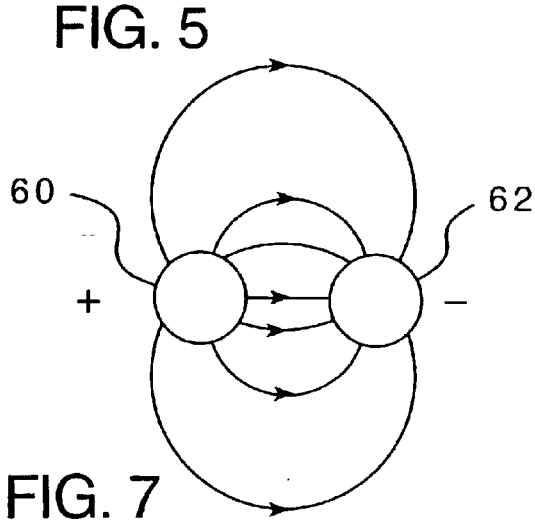
FIG. 7 illustrates a prior art form of dipole antenna and the corresponding current field.

Referring to the prior art dipole construction shown in FIG. 7, a pair of electrical conductors 60, 62 are positioned in relative spaced relationship and illustrate the current field exhibited by such construction. This shows that the majority of the current flux goes directly from the positive pole 60 to the negative pole 62, thereby providing a strong shorting current which not only wastes power, but also promotes tissue damages at the source site and other adverse effects which might interfere with a vital organ's activity, such as cardio-pulmonary, nervous or muscular functions. It is also noted that the use of far-field components of the antenna field, which contributes the transfer of information, is relatively weak.

While the individual shells 44, 46 may be symmetrical, in the preferred form of the invention, the shells 44, 46 are asymmetrical and have the upper portion which may be considered to be above the horizontal bisector between the lowermost portion and uppermost of the shell elongated with respect to the lower. This serves to provide the desired directional transmission.

Figure 8:
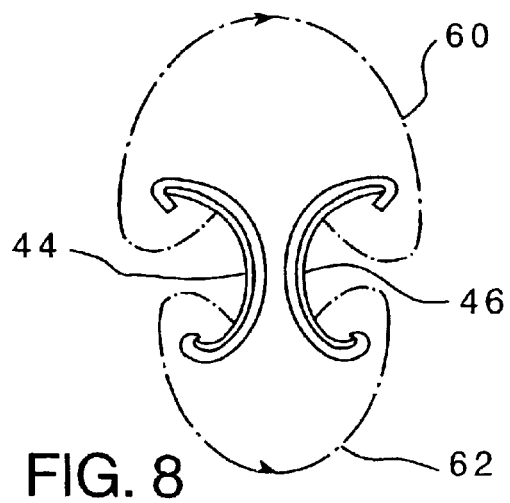
FIG. 8 illustrates a preferred form of volume conduction antenna of the present invention and its associated current flow.

Also shown in FIG. 8 is the fact that the generally x-shaped configuration of the antenna electrodes, combined with the insulators blocking short circuiting, force the current to flow around longer paths thereby increasing the far-field as the amount of current flowing through the conductor volume is the same in both FIGS. 7 and 8. The flux lines of the upper portion, as represented by reference number 60 are longer than the flux lines of the lower portions 62.

The preferred antenna, as shown in FIG. 8, will preferably be employed solely in the implanted first volume conductive antenna 8 and not in the external second antenna 20. A comparison between the x-shaped electrode pair, as shown in FIG. 8, was made with the known dipole antenna as shown in FIG. 7, wherein both antennas had a width of 7 mm. In each instance, the transmitted sinesoidal current signal was 1 KHz and the received voltage signal by the external electrodes 15 cms from the internal electrodes was measured. The results are shown in Table 1.

TABLE 1

| Received Signal | X-Shaped Volume Conductive Antenna | | | Dipole Antenna | | |
|---|---|---|---|---|---|---|
| Strength | Current | Voltage | Power | Current | Voltage | Power |
| 0.05 mV | 130 µA | 20 mV | 1.3 µW | 428 µA | 600 mV | 128.4 µW |
| 0.1 mV | 242 µA | 40 mV | 4.84 µW | 762 µA | 800 mV | 304.8 µW |
| 0.15 mV | 393 µA | 60 mV | 11.79 µW | 1133 µA | 1000 mV | 565.5 µW |

The first column shows the received signal strength in mV (peak value) for each three levels. The first column under each antenna heading indicates the required transmission current in µA (peak value), followed by the transmission voltage in mV (peak value) and power consumption in µW. It will be seen that for the same output, the new antenna required only about 30–35% of the transmission current, 3–6% of the transmission voltage and 1–2% of the power, as compared with the known prior design as shown in FIG. 7. These results confirm the fact that the present invention facilitates miniaturization, lower power consumption and longer battery life or the use of a smaller battery or other power source while preserving the desired communication efficiency.

Among the enhanced difficulties between the use of an internal device within a living patient and an external device effecting bi-directional communication therebetween are the fact that in a live biological body, there is a noisy environment due to the ongoing activity of heartbeat, arterial pulses and muscle activity, for example. Also, the internal and external devices must coordinate their data communication paths so as to provide for synchronized bidimensional communication while taking advantage of volume conduction characteristics of current pulse flow through live biological tissue. All of this must be accomplished employing an internal device which preferably is of small size, light weight and watertight.

A preferred way of accomplishing the foregoing in the present invention is to employ the electrocardiographic (ECG) signal as a clock for synchronization.

Figure 9:
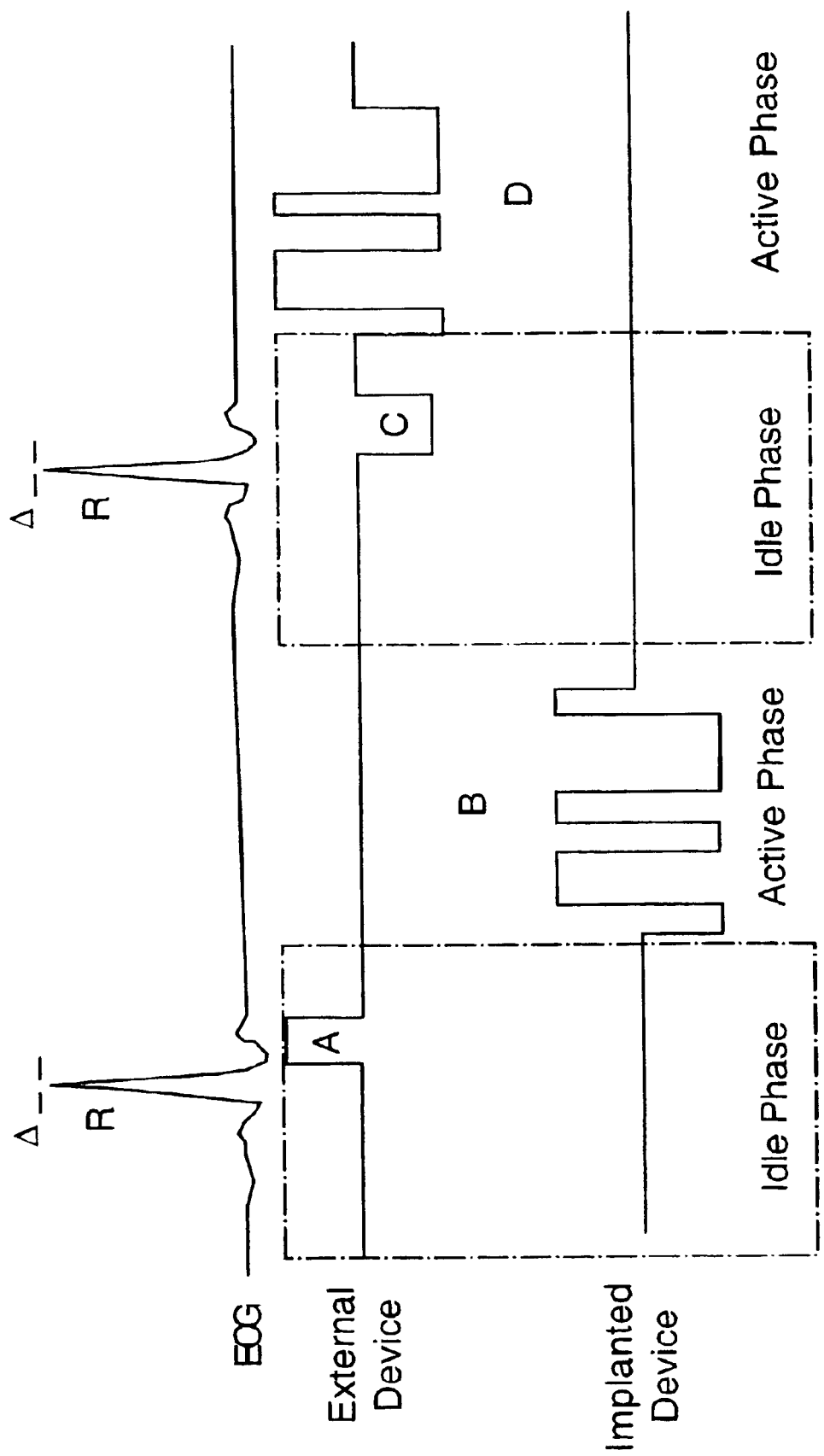
FIG. 9 illustrates schematically a preferred form of synchronizing the communication of the present invention with the heart action as monitored through an electrocardiogram.

Referring to FIG. 9, a time frame reference moving horizontally from left to right is provided graphically. As will be appreciated in the description which follows, use of the cardiac ECG as a reference, combined with exchange between the internal device and the external device facilitate: (1) providing efficient communication; (2) eliminating the need for an external clock mechanism which synchronizes the activities of the implanted device and external device; and (3) maximizing signal-to-noise ratio and, in particular, minimizing the noisy effect created by the heart pumping and deformation of major arteries.

Referring to FIG. 9, there is shown in the uppermost portion, the sharp peaks designated R-waves and shown as "R," with the delta symbol and two-spaced lines indicating that communication between the external device and internal device will not occur during that period. As a result of not communicating during the R-wave, this source of noise which has the potential to interfere with efficient communication between the external device and the internal device is avoided. Underlying the plot of the ECG are the plots of the external device and the implanted device. The initial Idle Phase has an R-wave followed by a positive pulse designated "A" which is transmitted by the external device to the implanted device during the idle phase. This current pulse is a request for the implanted device to transmit data. In response, a signal labeled "B" is sent by the implanted first antenna 8 to the external second antenna 20 (FIG. 1) during the Active Phase. This transmission/reception halts automatically after a certain predetermined period of time. If the data transmission has not been completed, a positive going pulse A is sent again upon the arrival of the next R-wave by the external device and the process repeats (not shown). If the external device would like to send commands or instructions to the internal device, a negative pulse, such as pulse "C" is sent by the external device during the Idle Phase after an R-wave. The implanted device then switches to the receiving mode and a signal wave labeled "D" is put on the channel by the external device during the quiescent period of the ECG in an Active Phase. It will be appreciated that the illustration in FIG. 9 is for conceptual purposes and in actual functioning the waveforms "A," "B," "C" and "D" would be modulated and well defined waveforms suitable for transmission through the communication channel to take advantage of the volume conduction.

Figure 10A:
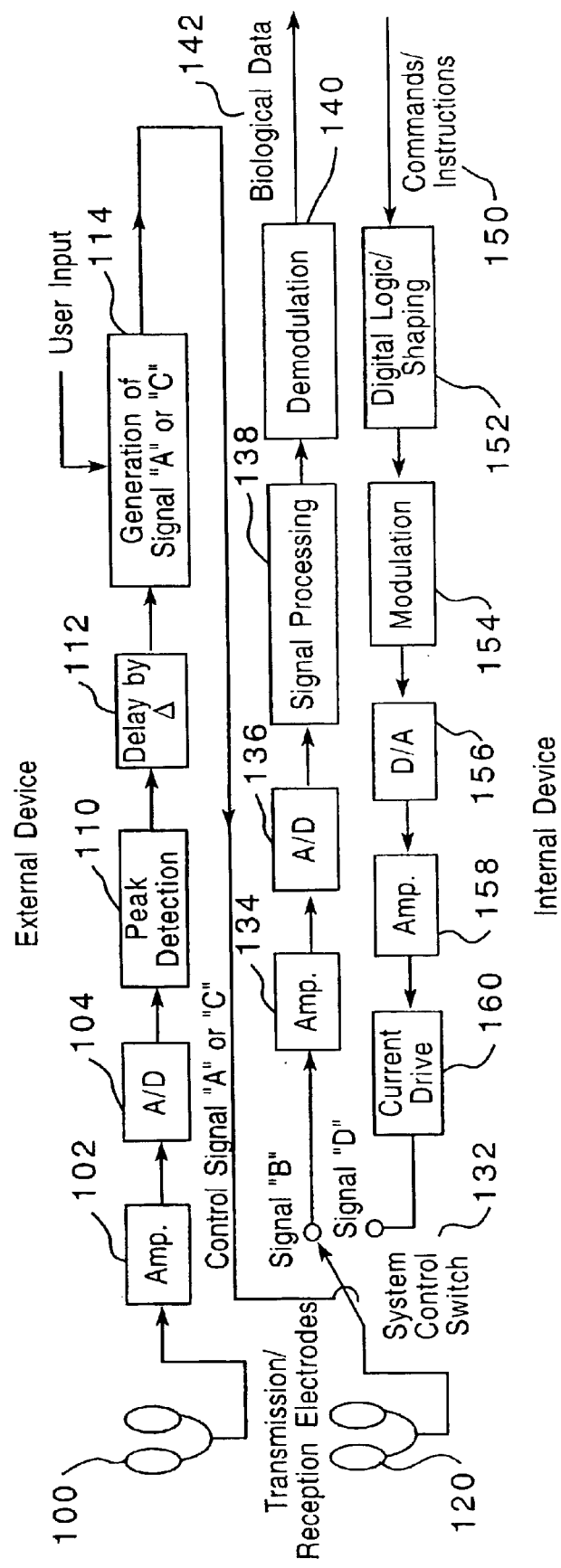
FIGS. 10(a) and 10(b) illustrate schematically the external and internal device functioning in the context of FIG. 9.
Figure 10B:
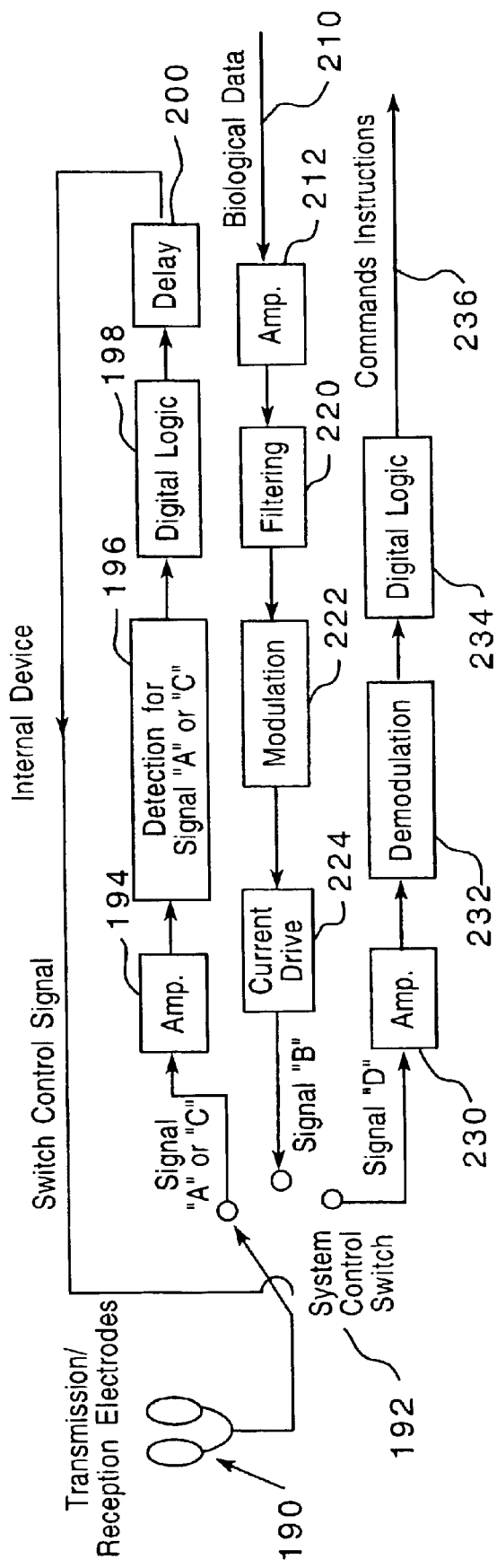

The flow diagrams of FIGS. 10(a) and 10(b) illustrate schematically flow diagrams of ways in which the concepts of FIG. 9 may be implemented in achieving the objectives of the present invention. More specifically, in monitoring the heart involvement, the second antenna has a pair of body surface electrodes 100 which receive the ECG signals which are amplified at 102 and converted into a digital equivalent at analog-to-digital converter (A/D) 104, followed by peak detection 110 delayed by the increment delta 112 and generation of signals "A" or "C" 114. The control signal is then introduced into the transmission/reception antenna electrodes 120 which, depending upon whether it is signal "B," meaning that it is the implanted device emitting the signal, or signal "D," meaning that it is the external device emitting the signal, an appropriate position of control switch 132 will be employed. If it is signal "B," there is amplification 134, analog-to-digital conversion 136, signal processing 138 in the microprocessor 22 (FIG. 1), demodulation 140 and the emitted biological data 142 which has been communicated. With the signal "D" emitted by the external device with a command signal 150 passing through the digital logic shaping station 152, followed by modulation 154 and digital-to-analog conversion 156, amplification 158 and current drive which provides an appropriate amount of power to be emitted by the skin-surface external electrodes 160.

Referring now to FIG. 10(b) and the implanted device, the implanted antenna shown as 8 in FIG. 1 represented by 190 in FIG. 10(b) has a system control switch 192, which, depending upon which of the four signals in the example shown in FIG. 9 is being employed will be in an appropriate position. If the signal is "A" or "C," it is amplified 194, is detected for a "A" or "C" 196, which is subjected to digital logic 198, which, after a desired delay 200, activates the switch 192. If the signal is "A," biological data 210, after amplification 212, filtering 220 and modulation 222, all in analog form, are sent to the electrodes by current driver 224 for transmission through drive signal "B." If the status is "C," signal "D" is received from the electrodes 190, is amplified 230, demodulated 232 and is converted to appropriate digital form and processed by digital logic 234, after which the suitable commands/instructions 236 are provided.

If desired, the system may be operated ignoring the peaks of the ECG for a specified number of R-waves. A further alternative would be to build a buffer and transmit each packet of data at a faster or slower rate than real-time, as desired for specific applications.

It will be appreciated that a central benefit of the present invention is the ability to transmit current pulses efficiently and synchronously through live biological tissues between implanted and external devices. The reduced size of the unit permits an encapsulated implantable device employing the benefits of microelectronic chips, for example, in the brain, torso, or abdomen or other portions of the body.

Figure 11:
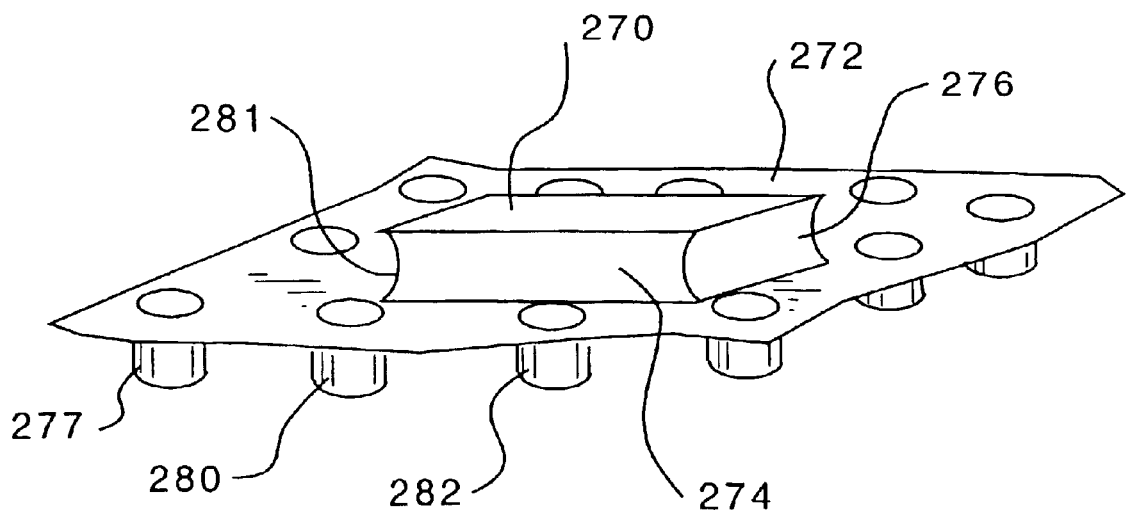
FIG. 11 illustrates a form of implantable brain chip design with a first antenna of the present invention having a pair of electrodes.
Figure 12:
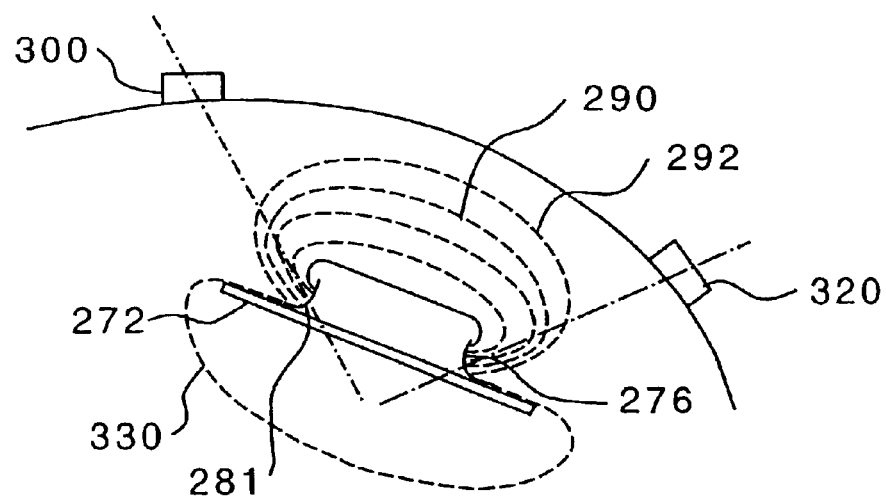
FIG. 12 illustrates schematically functioning of the electrodes of FIG. 11.

Referring to FIGS. 11 and 12, examples of a preferred use in respect of the brain will be considered.

In this embodiment, the implanted device or electronic capsule 270 includes an electrically insulative material 274 interposed between the electrodes 276, 281 of the first antenna. The implanted device is positioned on a flexible sheet 272, which may be plastic with an underlying plurality of subdural electrode contacts shown generally at 277, 280, 282, for example.

In this form of the implanted first antenna, a pair of outwardly concave electrodes 276, 281 are separated by the large electrically insulating element 274 which may contain or have secured thereto first circuit components. Unlike the embodiment shown in FIGS. 4–6 and 8, each electrode 276, 281, as viewed from an end such as perpendicular to electrode 276, for example, will appear to be generally rectangular.

The first antenna assembly may advantageously form part of an electronic chip which is encapsulated and implanted in the brain region between the skull and the brain. The flexible, transparent, thin plastic sheet 272 may be provided in a variety of sizes and shapes. Similar sheets are commercially available for subdural EEG recording during diagnosis of epilepsy. The connection lead and connector are removed so as to convert this system from wire transmission to wireless transmission. The first antenna electrode 276, 281, in the form illustrated, are altered in shape and size, but retain the beneficial properties of the type disclosed herein in FIGS. 4–6 and 8. It will be appreciated that the structure of FIG. 11 may be used for diagnostic and monitoring functions as by recording subdural EEG and may also be used therapeutically in stimulating the brain. The implanted device 270 may contain amplifiers, modulators and internal data communication subsystem, and a power source. The first antenna electrodes 276, 281, in the form shown, are integrated with the implanted device 270 at the ends thereof. These electrodes are externally concave and may be covered with a gold foil to establish the two x-electrode surfaces.

The implantable device 270 with the integrated first antenna electrodes 276, 281 preferably has a width of less than about 12 mm, a length of less than about 12 mm and a thickness of less than about 4 mm.

As shown in FIG. 12, the volume conduction first antenna 270, which has electrodes 276, 281, is a directional antenna with the emitted current pulses, as exemplified by lines 290, 292, being delivered generally in the direction of external second antenna electrodes 300, 320, which are in contact with the scalp. The plastic sheet 272 is flexible, thereby permitting it to be deformed freely to conform to the exterior shape of the cortex. In the case where the recording/stimulation task will be performed within a sulcus, a smaller flexible sheet with thinner contacts would be utilized to facilitate insertion into the sulcus. A further alternative would be to use nanotube material to construct stimulation/recording electrodes.

Among the advantages of the embodiment of FIGS. 11 and 12 are the use of a relatively large surface area at each x-antenna electrode piece, thereby reducing the current density in brain tissue surrounding the antenna electrodes and improving electrical contact with the electrically conductive fluid within the brain. It also increases the efficiency of the transmitter because of the larger separation, which may be on the order of 12 mm between the two electrode surfaces. It further eliminates the need for a stand alone antenna electrodes, thereby reducing the size of the implantable device and facilitating placement during neurosurgery. Further, the flexible sheet 272 functions as a reflector which strengthens the current field in direction of reception and weakens the current flowing from and into the brain. This latter feature is important, as it reduces the undesired brain stimulation as the brain current shown in the dashed curve designated 330 is smaller than the current in the direction of transmission.

While, for purposes of illustration herein, focus has been placed upon use of the present invention in respect of brain, torso, and abdominal introduction of the implanted device, it will be appreciated that a wide number of applications wherein an implantable device can communicate information and receive information through the advantageous use of volume conduction may be employed.

It will be appreciated that the present invention may be used for diagnostic and monitoring functions, as well as for therapeutic activity. For example, obtaining information regarding brain functioning, such as EEG and therapeutic use through energizing the electrodes in deep-brain stimulation such as described in respect of FIGS. 11 and 12, may be beneficially provided. Further, examples of utility are in epileptic seizure monitoring and intervention and bypassing brain signals to control limb movement for people with spinal cord injuries.

It will be appreciated, therefore, that the present invention provides a unique method and associated apparatus for efficiently having synchronized, two-way communication between an internal device and an external device through current pulse conduction through living biological tissues has been provided. The ionic fluid of biological tissue, such as cerebrospinal fluid, for example, is highly electrically conductive. Certain preferred features such as a highly efficient antenna which facilitates enhanced signal-to-noise ratio and directional delivery and receipt of signals are provided. In addition, certain noise reducing embodiments such as avoidance of the heart noise disturbances have also been provided.

Whereas particular embodiments of the invention have been described herein for purposes of illustration, it will be evident to those skilled in the art that numerous variations may be made without departing from the invention as set forth in the appended claims.

We claim:

1. A method of data communication between an implanted device and an external device comprising providing an implanted device having a first antenna and first circuit components operatively associated therewith, providing an external device having a second antenna and an associated microprocessor, positioning said first antenna and said second antenna with living biological tissue therebetween, effecting communication between said implanted device and said external device to establish current pulses through ionic fluid in said biological tissue in at least one direction between said first antenna electrode and said second antenna electrode, and effecting said communication in a synchronous manner.

2. The method of claim 1, including
implanting said implanted device in a living patient.
3. The method of claim 2, including
implanting said implanted device in a human being.
4. The method of claim 3, including
effecting said communication both from said first antenna to second antenna and from said second antenna to said first antenna.
5. The method of claim 4, including
implanting said implantable device in the abdomen of said human being.
6. The method of claim 4, including
placing the electrodes of said second antenna in contact with the skin of said human being.
7. The method of claim 4, including
providing a microprocessor as one of said first circuit components.
8. The method of claim 7, including
providing at least one sensor as one of said first circuit components.
9. The method of claim 8, including
said implanted device in the brain of said human being.
10. The method of claim 9, including
employing said method to monitor brain functioning.
11. The method of claim 10, including
employing said method to communicate subdural electro-encepholographic signals to said external device.
12. The method of claim 1, including
employing said method for diagnostic purposes.
13. The method of claim 1, including
employing said method for therapeutic purposes.
14. The method of claim 1, including
providing a power source as a said first circuit component in said implanted device.
15. The method of claim 1, including
directing the current pulses from said implanted first antenna through said biological material to said external second antenna.
16. The method of claim 1, including
employing said first antenna and said second antenna for both transmission and reception of said current pulses.

17. A method of data communication between an implanted device and an external device comprising
providing an implanted device having a first antenna and first circuit components operatively associated therewith,
providing an external device having a second antenna and an associated microprocessor,
positioning said first antenna and said second antenna with living biological tissue therebetween,
effecting communication between said implanted device and said external device to establish current pulses in at least one direction between said first antenna and said second antenna,
implanting said implanted device in a living patient,
implanting said implanted device in a human being,
effecting said communication both from said first antenna to second antenna and from said second antenna to said first antenna,
effecting said communication in a synchronous manner, and
employing heart pulses of said human being as a clock in synchronizing said communications.

18. A method of data communication between an implanted device and an external device comprising
providing an implanted device having a first antenna and first circuit components operatively associated therewith,
providing an external device having a second antenna and an associated microprocessor,
positioning said first antenna and said second antenna with living biological tissue therebetween,
effecting communication between said implanted device and said external device to establish current pulses in at least one direction between said first antenna electrode and said second antenna electrode, and
establishing the distance between said first antenna and said second antenna at less than about 15 cm.

19. A method of data communication between an implanted device and an external device comprising
providing an implanted device having a first antenna and first circuit components operatively associated therewith,
providing an external device having a second antenna and an associated microprocessor,
positioning said first antenna and said second antenna with living biological tissue therebetween,
effecting communication between said implanted device and said external device to establish current pulses in at least one direction between said first antenna electrode and said second antenna electrode, and
employing in said first antenna a pair of electrically conductive concave shells having their concave surfaces facing in generally opposed directions from each other.

20. The method of claim 19, including
said electrically conductive concave shells having generally concave surfaces facing each other, and
electrically insulating the convex surfaces of said electrically conductive shells of said first antenna from each other.

21. The method of claim 19, including
said shells being asymmetrical.

22. A method of data communication between an implanted device and an external device comprising
providing an implanted device having a first antenna and first circuit components operatively associated therewith,
providing an external device having a second antenna and an associated microprocessor,
positioning said first antenna and said second antenna with living biological tissue therebetween,
effecting communication between said implanted device and said external device to establish current pulses in at least one direction between said first antenna electrode and said second antenna electrode, and
providing said first circuit components on an electronic chip.

23. The method of claim 22, including
providing said implanted first antenna on said electronic chip.

24. The method of claim 23, including
positioning said first antenna up to about 15 cm from said second antenna.

25. The method of claim 22, including
providing an electrically nonconductive flexible sheet to reflect brain current flux and resist said fluid contacting said first antenna.

26. A method of data communication between an implanted device and an external device comprising
 providing an implanted device having a first antenna and first circuit components operatively associated therewith,
 providing an external device having a second antenna and an associated microprocessor,
 positioning said first antenna and said second antenna with living biological tissue therebetween,
 effecting communication between said implanted device and said external device to establish current pulses in at least one direction between said first antenna electrode and said second antenna electrode, and
 protectively encapsulating said implanted device with a resinous material.

27. A method of data communication between an implanted device and an external device comprising
 providing an implanted device having a first antenna and first circuit components operatively associated therewith,
 providing an external device having a second antenna and an associated microprocessor,
 positioning said first antenna and said second antenna with living biological tissue therebetween,
 effecting communication between said implanted device and said external device to establish current pulses in at least one direction between said first antenna electrode and said second antenna electrode, and
 said implantable device having a width of less than about 12 mm, a length of less than about 12 mm and a thickness of less than about 4 mm.

28. A method of data communication between an implanted device and an external device comprising
 providing an implanted device having a first antenna and first circuit components operatively associated therewith,
 providing an external device having a second antenna and an associated microprocessor,
 positioning said first antenna and said second antenna with living biological tissue therebetween,
 effecting communication between said implanted device and said external device to establish current pulses in at least one direction between said first antenna electrode and said second antenna electrode,
 implanting said implanted device in a living patient,
 implanting said implanted device in a human being,
 effecting said communication both from said first antenna to second antenna and from said second antenna to said first antenna,
 providing a microprocessor as one of said first circuit components,
 providing at least one sensor as one of said first circuit components, and
 employing said external device to transmit a current pulse to cause said internal device to transmit data,
 said internal device responsively transmitting said data to said external device, and
 said transmissions being effected at times other than the period of R-waves of an electrocardiogram.

29. The method of claim 28 including
 said external device emitting a current pulse or pulses of the different sign or configuration from the pulses it emits when it requests data from said implanted device when it wishes to transmit data to said implanted device, and
 said external device following said pulses with the desired transmitted data to said implanted device with said pulses being transmitted at a time other than the time period when R-waves of the electrocardiogram are present.

30. Apparatus for volume conduction between an implantable device and an external device, comprising
 an implantable device having a first antenna and first circuit components for transmitting current pulses through living biological tissue and receiving current pulses therethrough,
 a second antenna for transmitting current pulses through living biological tissue and receiving current therethrough,
 said first circuit components including a first microprocessor,
 said external device having a second microprocessor,
 said first antenna being a directional antenna, and
 said apparatus being structured for directional data communication.

31. The apparatus of claim 30, including
 employing in said first antenna electrodes having a pair of electrically conductive concave shells facing in generally opposed directions from each other, and
 said second antenna for contacting the skin generally adjacent said biological tissue.

32. The apparatus of claim 31, including
 said antenna electrodes being asymmetrical.

33. The apparatus of claim 31, including
 said first circuit components including at least one sensor.

34. The apparatus of claim 33, including
 said implantable device structured to deliver EEG data to said external device.

35. The apparatus of claim 34, including
 said antenna electrode shells having convex surfaces generally facing each other, and
 electrical insulation disposed on said convex surfaces.

36. The apparatus of claim 34, including
 said first circuit components including at least one power source.

37. The apparatus of claim 30, including
 said implantable device being configured and dimensioned to be implantable in a human abdomen.

38. The apparatus of claim 37, including
 said implantable device having a width less than about 12 mm, a length less than about 12, and a thickness less than about 4 mm.

39. The apparatus of claim 36, including
 an electrically nonconductive flexible sheet for reflecting brain current flux away from said first antenna disposed on the opposite side of said first antenna electrode from said second antenna.

* * * * *

UNITED STATES PATENT AND TRADEMARK OFFICE
CERTIFICATE OF CORRECTION

PATENT NO. : 6,847,844 B2
DATED : January 25, 2005
INVENTOR(S) : Mingui Sun et al.

It is certified that error appears in the above-identified patent and that said Letters Patent is hereby corrected as shown below:

<u>Column 9,</u>
Line 23, insert -- implanting -- prior to the first occurrence of "said".

Signed and Sealed this

Sixteenth Day of August, 2005

JON W. DUDAS
*Director of the United States Patent and Trademark Office*